US 6,607,492 B2

(12) United States Patent
Ogura (10) Patent No.: US 6,607,492 B2
(45) Date of Patent: Aug. 19, 2003

(54) PRESSURE-PULSE-WAVE DETECTING APPARATUS (75) Inventor: Toshihiko Ogura, Komaki (JP)

(73) Assignee: Colin Corporation, Komaki (JP)

(*) Notice: Subject to any disclaimer, the term of this patent is extended or adjusted under 35 U.S.C. 154(b) by 34 days.

(21) Appl. No.: 10/014,561

(22) Filed: Dec. 14, 2001

(65) Prior Publication Data
US 2002/0143260 A1 Oct. 3, 2002

(30) Foreign Application Priority Data
Mar. 30, 2001 (JP) ........................................ 2001-098401

(51) Int. Cl.[7] .................................................. A61B 5/00
(52) U.S. Cl. ........................ 600/485; 600/500; 600/504
(58) Field of Search ................................. 600/485, 490, 600/453–456, 500–503, 504

(56) References Cited

U.S. PATENT DOCUMENTS 5,715,826 A    2/1998  Horrocks et al.
5,727,561 A  * 3/1998  Owsley ....................... 600/504
6,099,478 A  * 8/2000  Aoshima et al. ............ 600/500
6,129,676 A  * 10/2000 Odagiri et al. .............. 600/500

FOREIGN PATENT DOCUMENTS

EP    0 818 176 A1    1/1998
EP    1 053 714 A2   11/2000

* cited by examiner

Primary Examiner—Robert L. Nasser
(74) Attorney, Agent, or Firm—Oliff & Berridge, PLC (57) ABSTRACT An apparatus for detecting a pressure pulse wave produced by an artery of a living subject, including a pressure-pulse-wave sensor which is adapted to be pressed against the artery of the subject via a skin of the subject, detects the pressure pulse wave produced by the artery, and generates a pressure-pulse-wave signal representing the detected pressure pulse wave, a band-pass filter which extracts, from the pressure-pulse-wave signal, a blood-flow-noise signal having frequencies in a prescribed blood-flow-noise frequency range, and an output device which outputs the blood-flow-noise signal extracted by the band-pass filter.

10 Claims, 6 Drawing Sheets

PRESSURE-PULSE-WAVE DETECTING APPARATUS

BACKGROUND OF THE INVENTION

1. Field of the Invention

The present invention relates to a pressure-pulse-wave detecting apparatus which includes a pressure-pulse-wave sensor adapted to be pressed against an artery of a living subject via a skin of the subject.

2. Related Art Statement

In some cases, it is needed to detect a pulse wave from a large-diameter artery of a patient, such as a carotid artery or a brachial artery, so as to monitor a dynamic circulatory condition of the patient and thereby make a diagnosis thereon. In those cases, a pressure-pulse-wave detecting apparatus is widely used which presses the artery via the skin and detects a pressure pulse wave, i.e., a pressure oscillation that is produced by the artery and is propagated to the skin. Since the pressure-pulse-wave detecting apparatus can non-invasively detect the pulse wave, it can reduce the discomfort the patient feels.

When the pressure-pulse-wave detecting apparatus is used to detect the pressure pulse wave, it is needed to press a portion of the artery to some degree. However, that portion of the artery may suffer stenosis or arteriostenosis because of, e.g., arteriosclerosis. If the portion of the artery that suffers arteriostenosis and accordingly cannot allow a normal flow of blood, is pressed by the apparatus, the flow of blood is more strongly blocked to disadvantage. Meanwhile, in the case where a portion of an artery that suffers stenosis because of sclerosing plaque, is pressed, the plaque may be broken, and blood clots may outflow and generate thrombus on the downstream side. Thus, it is needed to detect a pressure pulse wave from a portion of an artery that is free of stenosis. However, the conventional pressure-pulse-wave detecting apparatus cannot judge whether an artery suffers stenosis or not.

SUMMARY OF THE INVENTION

It is therefore an object of the present invention to provide a pressure-pulse-wave detecting apparatus which makes it possible to judge whether a portion of an artery from which a pressure pulse wave is to be detected thereby suffers stenosis.

The Inventor has carried out extensive studies to achieve the above object and found that an artery which suffers stenosis causes a turbulent flow of blood and a pressure-pulse-wave signal obtained from the artery contains a signal component (hereinafter, referred to as the "blood-flow-noise signal") having frequencies characteristic of the turbulent flow. Therefore, if the blood-flow-noise signal is extracted from the pressure-pulse-wave signal, it is possible to judge, from a magnitude of the blood-flow-noise signal, whether a portion of an artery from which a pressure pulse wave is to be detected suffers stenosis. The present invention has been developed based on this finding.

The above object has been achieved by the present invention. According to a first aspect of the present invention, there is provided an apparatus for detecting a pressure pulse wave produced by an artery of a living subject, comprising a pressure-pulse-wave sensor which is adapted to be pressed against the artery of the subject via a skin of the subject, detects the pressure pulse wave produced by the artery, and generates a pressure-pulse-wave signal representing the detected pressure pulse wave; a band-pass filter which extracts, from the pressure-pulse-wave signal, a blood-flow-noise signal having frequencies in a prescribed blood-flow-noise frequency range; and an output device which outputs the blood-flow-noise signal extracted by the band-pass filter.

According to this aspect, the band-pass filter extracts, from the pressure-pulse-wave signal, the blood-flow-noise signal, and the output device outputs the blood-flow-noise signal. Therefore, an operator such as a doctor or a nurse can judge, from a magnitude of the blood-flow-noise signal given by the output device, whether a portion of the artery that is pressed by the apparatus suffers stenosis.

According to a second aspect of the present invention, there is provided an apparatus for detecting a pressure pulse wave produced by an artery of a living subject, comprising a pressure-pulse-wave sensor which is adapted to be pressed against the artery of the subject via a skin of the subject, detects the pressure pulse wave produced by the artery, and generates a pressure-pulse-wave signal representing the detected pressure pulse wave; a band-pass filter which extracts, from the pressure-pulse-wave signal, a blood-flow-noise signal having frequencies in a prescribed blood-flow-noise frequency range; a blood-flow-noise-information obtaining means for obtaining blood-flow-noise information representing a magnitude of the blood-flow-noise signal extracted by the band-pass filter; and an output device which outputs the blood-flow-noise information obtained by the blood-flow-noise-information obtaining means.

According to this aspect, the band-pass filter extracts, from the pressure-pulse-wave signal, the blood-flow-noise signal, the blood-flow-noise-information obtaining means obtains blood-flow-noise information representing a magnitude of the blood-flow-noise signal, and the output device outputs the blood-flow-noise information. Therefore, the operator can judge, from the magnitude represented by the blood-flow-noise information, whether a portion of the artery that is pressed by the apparatus suffers stenosis.

According to a third aspect of the present invention, there is provided an apparatus for detecting a pressure pulse wave produced by an artery of a living subject, comprising a pressure-pulse-wave sensor which is adapted to be pressed against the artery of the subject via a skin of the subject, detects the pressure pulse wave produced by the artery, and generates a pressure-pulse-wave signal representing the detected pressure pulse wave; a band-pass filter which extracts, from the pressure-pulse-wave signal, a blood-flow-noise signal having frequencies in a prescribed blood-flow-noise frequency range; a stenosis judging means for making, based on a magnitude of the blood-flow-noise signal extracted by the band-pass filter, a judgment about whether a portion of the artery that is pressed by the pressure-pulse-wave sensor suffers stenosis; and an output device which outputs the judgment made by the stenosis judging means.

According to this aspect, the band-pass filter extracts, from the pressure-pulse-wave signal, the blood-flow-noise signal, the stenosis judging means makes, based on the magnitude of the blood-flow-noise signal, the judgment about whether the portion of the artery that is pressed by the apparatus suffers stenosis, and the output device outputs the judgment. Therefore, the operator can easily know about whether the portion of the artery that is pressed by the apparatus suffers stenosis.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Hereinafter, there will be described an embodiment of the present invention in detail by reference to the drawings.

Figure 1:
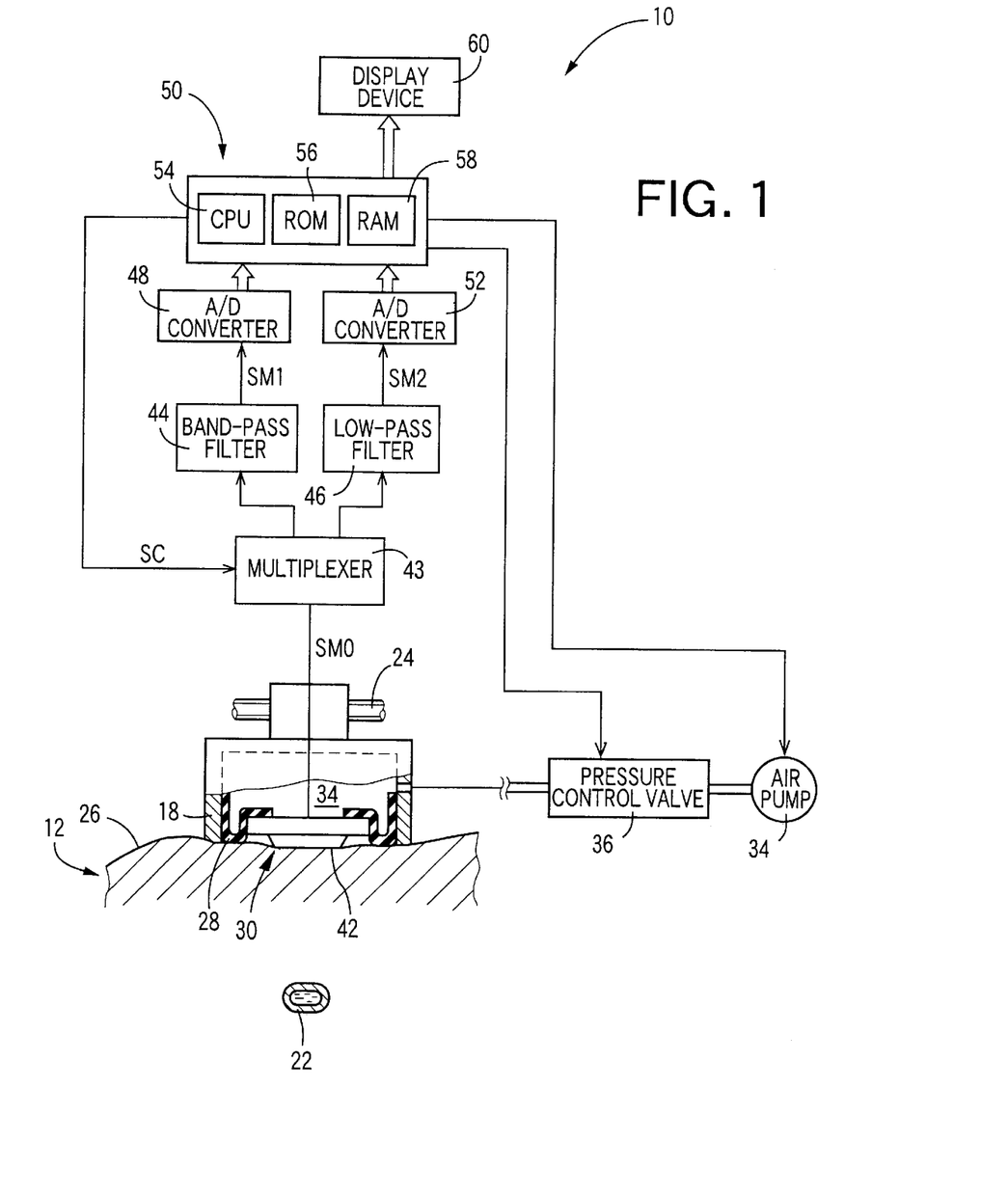
FIG. 1 is a diagrammatic view of a construction of a carotid-pulse-wave detecting apparatus to which the present invention is applied.

FIG. 1 shows a diagrammatic view of a construction of a carotid-pulse-wave detecting apparatus 10 to which the present invention is applied. The carotid-pulse-wave detecting apparatus 10 functions as a pressure-pulse-wave detecting apparatus which detects a pressure pulse wave from a neck portion 12 of a patient as a living subject.

Figure 2:
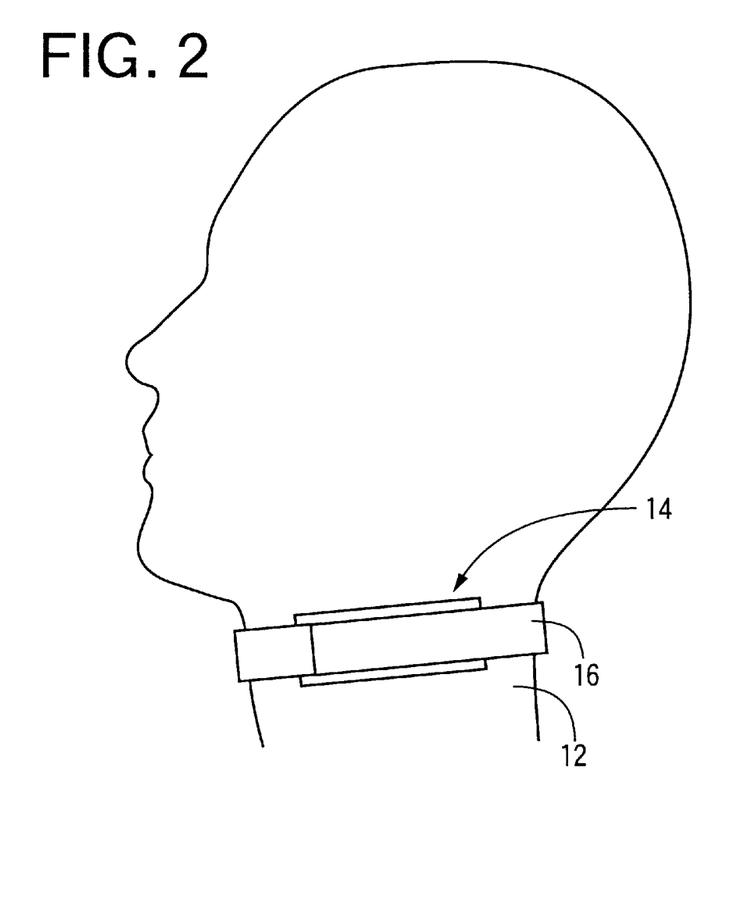
FIG. 2 is a view showing a state in which a pressure-pulse-wave detecting probe of the apparatus of FIG. 1 is worn on a neck portion of a patient.
Figure 3:
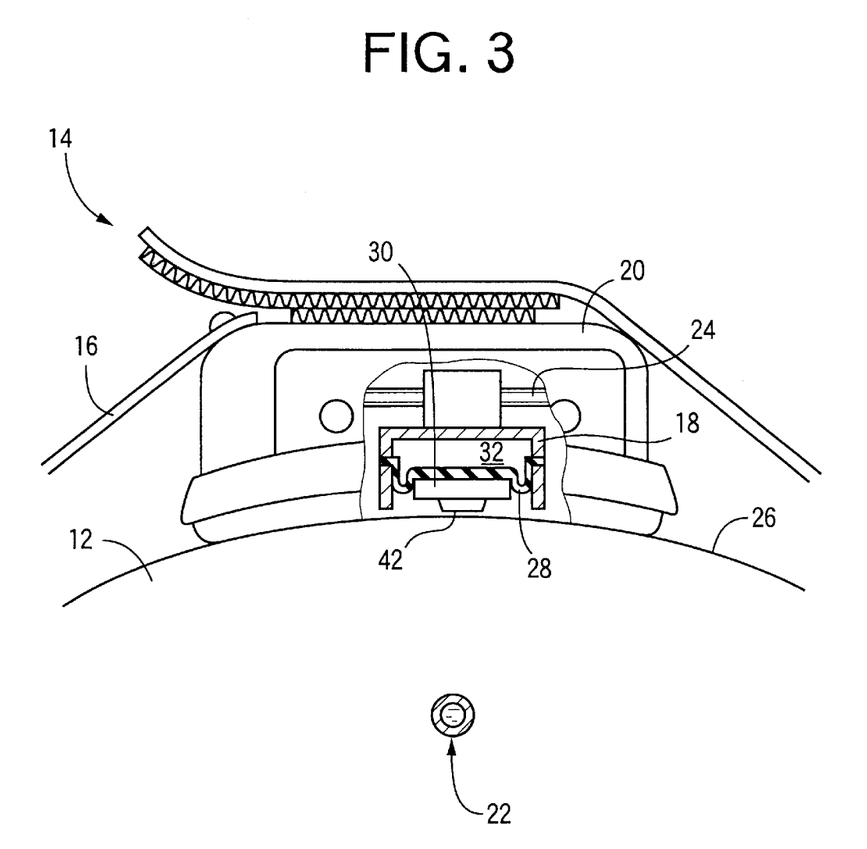
FIG. 3 is a partly-cut-away view of the pressure-pulse-wave detecting probe of FIG. 2.

The carotid-pulse-wave detecting apparatus 10 includes a pressure-pulse-wave detecting probe 14 whose construction is illustrated in detail in FIG. 3. As shown in FIG. 2, the pressure-pulse-wave detecting probe 14 is worn on the neck portion 12 with the help of a fastening band 16. As shown in detail in FIG. 3, the pressure-pulse-wave detecting probe 14 includes a container-like sensor housing 18; a case 20 which accommodates the sensor housing 18; and a feed screw 24 which is threadedly engaged with the sensor housing 18 and is rotated by an electric motor, not shown, provided in the case 20 so as to move the sensor housing 18 in a widthwise direction of a carotid artery 22. With the help of the fastening band 16 connected to the case 20, the case 20 is detachably attached to the neck portion 12 of the subject, such that an open end of the sensor housing 18 is opposed to a body surface 26 of the neck portion 12.

In addition, the detecting probe 14 includes a pressure-pulse-wave sensor 30 which is secured via a diaphragm 28 to an inner wall of the sensor housing 18, such that the sensor 30 is movable relative to the housing 18 and is advanceable out of the open end of the same 18. The sensor housing 18, the diaphragm 28, etc. cooperate with one another to define a pressure chamber 32, which is supplied with a pressurized air from an air pump 34 via a pressure-control valve 36, as shown in FIG. 1, so that the pressure-pulse-wave sensor 30 is pressed against the body surface 26 with a pressing force corresponding to the air pressure (Pa) in the pressure chamber 32. Thus, the pressing force applied to the sensor 30 is expressed in terms of the air pressure (mmHg) in the chamber 32.

The sensor housing 18 and the diaphragm 28 cooperate with each other to provide a pressing device 38 which presses the pressure-pulse-wave sensor 30 against the carotid artery 22, and the feed screw 24 and the not-shown motor cooperate with each other to provide a pressing-position changing device or a widthwise-direction moving device 40 which moves the pressure-pulse-wave sensor 30 in the widthwise direction of the carotid artery 22 and thereby changes a pressing position where the sensor 30 is pressed on the body surface 26.

Figure 4:
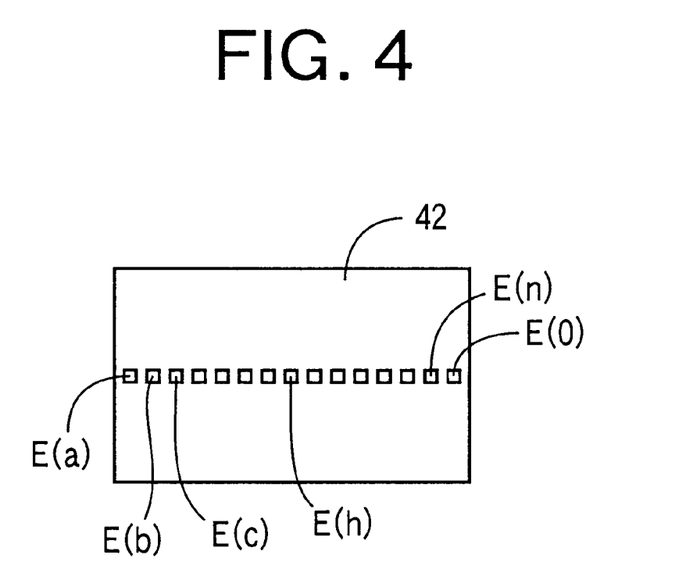
FIG. 4 is a view showing a state in which an array of pressure-sensing elements are provided in a pressing surface of a pressure-pulse-wave sensor of the probe of FIG. 2.

The pressure-pulse-wave sensor 30 includes a semiconductor chip which is provided by, e.g., a monocrystalline silicon and has a pressing surface 42; and fifteen semiconductor pressure-sensing elements (hereinafter, referred to as "the pressure-sensing elements") E(a), E(b), . . . , E(o) which are arranged, as shown in FIG. 4, in the pressing surface 42 at a regular interval (e.g., about 0.6 mm) in the widthwise direction of the carotid artery 22, i.e., in the direction of movement of the sensor 30 parallel to the feed screw 24, over a length greater than the diameter of the carotid artery 22.

The pressure-pulse-wave detecting probe 14, constructed as described above, is pressed against the body surface 26 of the neck portion 12 right above the carotid artery 22, so that the pressure-pulse-wave sensor 30 detects a pressure pulse wave, i.e., an oscillatory pressure wave which is produced from the carotid artery 22 and is propagated to the body surface 26, and supplies a pressure-pulse-wave signal SM0 representing the pressure pulse wave, to a multiplexer 43.

The multiplexer 43 sequentially supplies, according to respective switch signals SC supplied thereto from a control device 50, described later, respective prescribed lengths of the respective pressure-pulse-wave signals SM0 supplied thereto from the fifteen pressure-sensing elements E of the pressure-pulse-wave sensor 30, to each of a band-pass filter 44 and a low-pass filter 46.

The band-pass filter 44 is provided by an analog-signal processing circuit including a capacitor and a coil or a resistor. The band-pass filter 44 extracts, from each pressure-pulse-wave signal SM0, a signal component (i.e., a blood-flow-noise signal) having frequencies in a prescribed frequency range (e.g., from 200 to 600 Hz) corresponding to frequencies of noise produced by blood flow, and supplies a blood-flow-noise signal SM1 to the control device 50 via an analog-to-digital (A/D) converter 48. Since the band-pass filter 44 sequentially receives, via the multiplexer 43, the respective pressure-pulse-wave signals SM0 supplied from the fifteen pressure-sensing elements E, the band-pass filter 44 sequentially supplies the respective blood-flow-noise signals SM1 extracted from the fifteen pressure-pulse-wave signals SM0, to the control device 50.

Like the band-pass filter 44, the low-pass filter 46 is provided by an analog-signal processing circuit including a capacitor and a coil or a resistor. The low-pass filter 46 extracts, from each pressure-pulse-wave signal SM0, a signal component (hereinafter, referred to as the carotid-pulse-wave signal) SM2 representing a carotid pulse wave, and supplies the carotid-pulse-wave signal SM2 to the control device 50 via an A/D converter 52. Since the carotid pulse wave is a physical signal having a period equal to that of heartbeat of the patient, the low-pass filter 46 is so constructed as to extract, from each pressure-pulse-wave signal SM0, a signal component having frequencies lower than, e.g., 50 Hz. In addition, since the low-pass filter 46 sequentially receives, via the multiplexer 43, the respective pressure-pulse-wave signals SM0 supplied from the fifteen pressure-sensing elements E, the filter 46 sequentially supplies the respective carotid-pulse-wave signals SM2 extracted from the fifteen pressure-pulse-wave signals SM0, to the control device 50.

The control device 50 is provided by a so-called microcomputer including a central processing unit (CPU) 54, a read only memory (ROM) 56, a random access memory (RAM) 58 and an input-and-output (I/O) port, not shown. The CPU 54 processes signals according to the control programs pre-stored in the ROM 56 by utilizing the temporary-storage function of the RAM 58, and supplies drive signals via the I/O port to respective drive circuits, not shown, associated with the pressure control valve 36 and the air pump 34 so as to control the air pressure in the pressure chamber 32. In addition, the CPU 54 supplies, to the multiplexer 43, each switch signal SC at a prescribed period sufficiently shorter than the period of heartbeat of the patient. Moreover, the CPU 54 operates a display device 60 to display a carotid-pulse-wave signal SM2 supplied from the low-pass filter 46 and a blood-flow-noise signal SM1 supplied from the band-pass filter 44. In addition, the CPU 54 judges, based on the blood-flow-noise signal SM1, whether a portion of the carotid artery 22 that is pressed by the pressure-pulse-wave sensor 30 suffers stenosis, and operates the display device 60 to display a result of this judgment.

Figure 5:
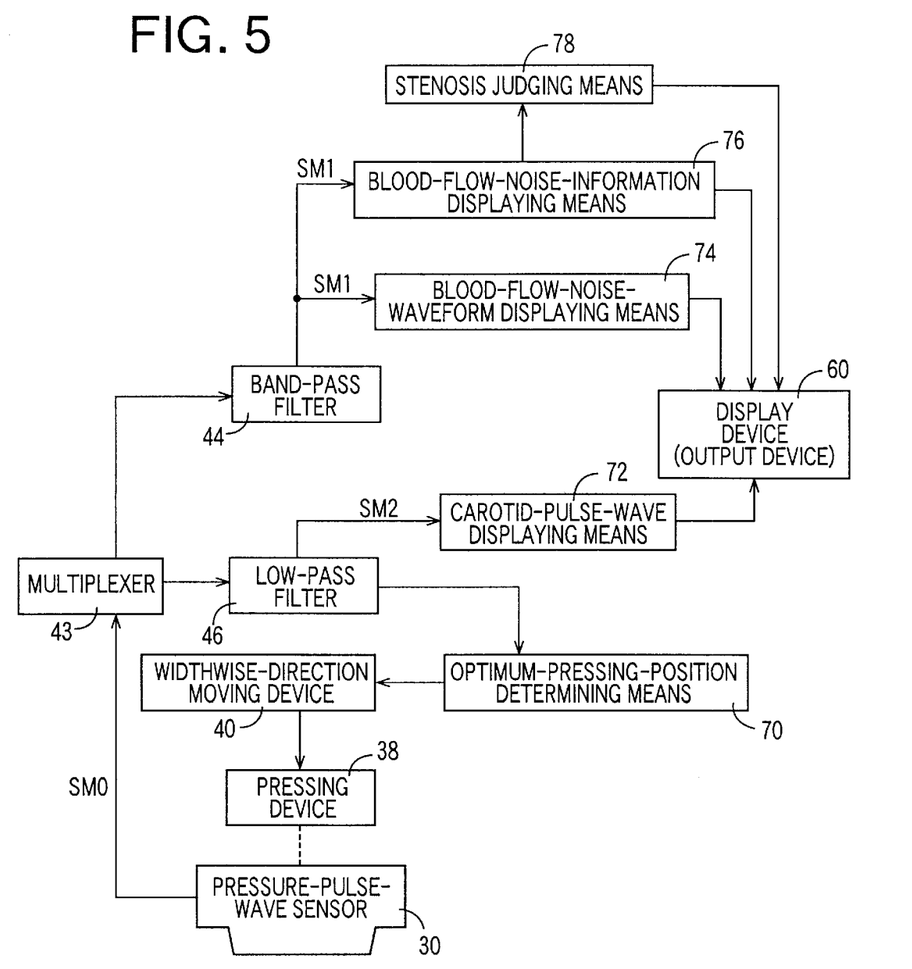
FIG. 5 is a block diagram for explaining essential functions of a control device of the carotid-pulse-wave detecting apparatus of FIG. 1.

FIG. 5 is a block diagram for explaining essential functions of the control device 50. In FIG. 5, an optimum-pressing-position determining means 70 initially judges, for the purpose of determining a pressing position where the pressure-pulse-wave sensor 30 is to be pressed, whether a prescribed pressing-position changing condition is satisfied, i.e., whether one Em of the pressure-sensing elements E arranged on the pressing surface 42 of the sensor 30 that detects the greatest one of respective amplitudes of the carotid pulse waves (i.e., the carotid-pulse-wave signals SM2) detected by all the pressure-sensing elements is located in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the two elements E located at the opposite ends of the array. The length or number is prescribed based on the diameter of the artery (i.e., the carotid artery 22) to be pressed by the pressure-pulse-wave sensor 30, and may be one fourth of the diameter. When this pressing-position changing condition is satisfied, the optimum-pressing-position determining means 70 carries out a pressing-position changing operation, as follows: After the pressing device 38 once moves the pressure-pulse-wave sensor 30 away from the body surface 26, the widthwise-direction moving device 40 moves the pressing device 38 and the sensor 30 over a prescribed distance, and then the pressing device 38 again presses the sensor 30 with a prescribed pressing force HDP1 that is sufficiently lower than a diastolic blood pressure of the artery (i.e., the carotid artery 22) to be pressed by the sensor 30. In this state, the determining means 70 judges again whether the prescribed pressing-position changing condition is satisfied. The determining means 70 repeats carrying out the operation and making the judgment till the pressing-position changing condition is not met any longer, preferably till the pressure-sensing element Em detecting the greatest amplitude is located in a prescribed middle portion of the array of elements E.

A carotid-pulse-wave displaying means 72 operates the display device 60 to display, in a prescribed display area of a two-dimensional screen thereof, a carotid pulse wave, i.e., a waveform of a carotid-pulse-wave signal SM2 supplied from the low-pass filter 46. A blood-flow-noise-waveform displaying means 74 operates the display device 60 to display, in another prescribed display area, a waveform of a blood-flow-noise signal SM1 supplied from the band-pass filter 44, such that a magnitude of the waveform of the blood-flow-noise signal SM1 can be compared, by an operator such as a doctor or a nurse, with a magnitude of waveform of the carotid-pulse-wave signal SM2 displayed by the carotid-pulse-wave displaying means 72. Thus, the display device 60 functions as an output device. If a portion of the carotid artery 22 that is pressed by the pressure-pulse-wave sensor 30 suffers stenosis, the blood-flow-noise signal SM1 shows a great magnitude. In addition, as compared with the case where the pressed portion of the carotid artery 22 does not suffer stenosis, the blood-flow-noise signal SM1 shows a great magnitude relative to the magnitude of the carotid-pulse-wave signal SM-2. Therefore, the operator can judge, from the magnitude of the blood-flow-noise signal SM1 displayed on the display device 60, or by comparing the magnitude of the blood-flow-noise signal SM1 with that of the carotid-pulse-wave signal SM2, whether the pressed portion of the carotid artery 22 suffers stenosis.

A blood-flow-noise-information obtaining means 76 obtains blood-flow-noise information representing a magnitude of a blood-flow-noise signal SM1 extracted by the band-pass filter 44, and operates the display device 50 to display the thus obtained blood-flow-noise information. The blood-flow-noise information may be the greatest magnitude of a prescribed length (e.g., from one heartbeat-synchronous pulse to ten heartbeat-synchronous pulses) of the blood-flow-noise signal SM1; an area defined by a prescribed length of the blood-flow-noise signal SM1; or an average magnitude of a prescribed length of the blood-flow-noise signal SM1. In addition, in the case where the blood-flow-noise signal SM1 is subjected to a frequency analysis, e.g., is transformed by Fourier transform into a function in which frequency is a variable, the blood-flow-noise information may be the greatest value of, or an area defined by, a waveform of the frequency-analyzed signal. If the portion of the carotid artery 22 pressed by the pressure-pulse-wave sensor 30 suffers stenosis, the blood-flow-noise signal SM1 shows a great magnitude and accordingly the blood-flow-noise information shows a great value.

A stenosis judging means 78 judges that the portion of the carotid artery 22 pressed by the pressure-pulse-wave sensor 30 suffers stenosis, when the blood-flow-noise information obtained by the blood-flow-noise-information obtaining means 76 is greater than a prescribed reference value. The stenosis judging means 78 operates the display device 60 to display characters or symbols indicating that the pressed portion of the artery 22 suffers stenosis.

Figure 6:
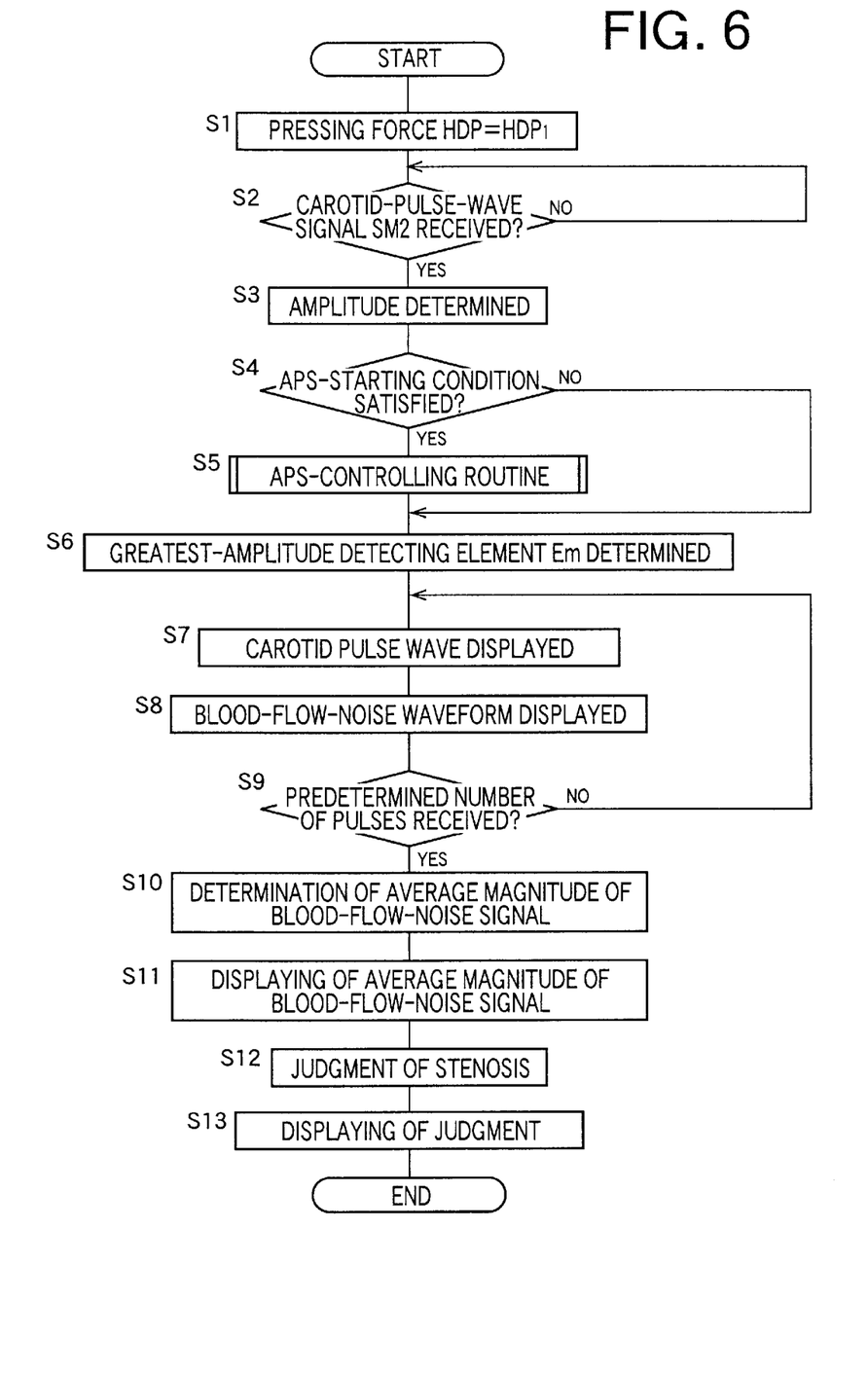
FIG. 6 is a flow chart representing a control program according to which the control device shown in the block diagram of FIG. 5 is operated.

FIG. 6 is a flow chart representing the control functions of the control device 50 shown in FIG. 5. The routine represented by the flow chart is carried out when the pressure-pulse-wave detecting probe 14 is worn on the neck portion 12 and before a carotid pulse wave is continuously detected by the probe 14.

First, the control device 50 carries out Step S1 (hereinafter, "Step" is omitted, if appropriate) to S5 that correspond to the optimum-pressing-position determining means 70. At S1, the control device 50 operates the pressing device 38 to change the pressure in the pressure chamber 32 so that the pressing force HDP applied to the pressure-pulse-wave sensor 30 is increased up to a prescribed pressing force HDP1 lower than a diastolic blood pressure of the carotid artery 22. Then, at S2, the control device 50 judges whether the control device 50 has received one heartbeat-synchronous pulse of each of the respective carotid-pulse-wave signals SM2 sequentially supplied via the low-pass filter 46 from the fifteen pressure-sensing elements E. So long as a negative judgment is made at S2, S2 is repeated.

Meanwhile, if a positive judgment is made at S2, the control goes to S3 where the control device 50 determines, for each of the fifteen pressure-sensing elements E, an amplitude of carotid pulse wave by subtracting, from a maximal magnitude of the one pulse of the carotid-pulse-wave signal SM2 supplied from the each element E, a minimum magnitude of the same pulse. Then, at S4, the control device 50 selects, based on the respective carotid-pulse-wave amplitudes determined at S3 for the elements E, one Em of the elements E that detects the greatest amplitude of all the amplitudes, and judges whether the prescribed pressing-position changing condition (i.e., APS-starting condition) is satisfied, i.e., whether the element Em detecting the greatest amplitude is located in one of the prescribed opposite end portions of the array of elements E. A negative judgment made at S4 indicates that the sensor 30 is positioned at the optimum pressing position and accordingly need not be moved, so that the control directly goes to S6 and the following steps, described later.

On the other hand, if a positive judgment is made at S4, that is, if the pressing position where the pressure-pulse-wave sensor 30 is pressed against the carotid artery 22 is not appropriate, the control proceeds with S5, i.e., an APS-controlling routine. According to this APS-controlling routine, the control device 50 determines the optimum pressing position where the element E located at substantially the middle of the array of elements E detects the greatest amplitude, that is, where the element Em detecting the greatest amplitude is located at substantially the middle of the array of elements E. To this end, the control device 50 operates the pressing device 38 and the widthwise-direction moving device 40 to once move the pressure-pulse-wave sensor 30 away from the body surface 26, move the pressing device 38 and the sensor 30 over a prescribed distance, and again press the sensor 30 with the prescribed pressing force HDP1. In this state, the control device 50 carries out steps identical with S2 and S3 to determine respective amplitudes and judge whether the element Em detecting the greatest amplitude is located at substantially the middle of the array of elements E. S4 and S5 are repeated till a positive judgment is made.

Thus, the control device 50 positions, at S2 to S5, the pressure-pulse-wave sensor 30 at the optimum pressing position. Then, the control goes to S6 to determine the element Em detecting the greatest amplitude in this state, as a greatest-amplitude detecting element Em.

Then, the control goes to S7 corresponding to the carotid-pulse-wave displaying means 72. At S7, the control device 50 operates the display device 60 to display, in a prescribed display area, the carotid-pulse-wave signal SM2 (i.e., the carotid pulse wave) continuously supplied via the low-pass filter 46 from the greatest-amplitude detecting element Em of the pressure-pulse-wave sensor 30, determined at S6. Then, at S8 corresponding to the blood-flow-noise-waveform displaying means 74, the control device 50 operates the display device 60 to display, in another prescribed display area, the blood-flow-noise signal SM1, i.e., waveform of blood-flow noise, that is continuously supplied via the band-pass filter 44 from the greatest-amplitude detecting element Em determined at S6.

Subsequently, at S9, the control device 50 judges whether the control device 50 has received a prescribed number (e.g., five) of heartbeat-synchronous pulses of each of the carotid-pulse-wave signal SM2 and the blood-flow-noise signal SM1 supplied from the greatest-amplitude detecting element Em determined at S6. If a length of a waveform of each of the carotid-pulse-wave signal SM2 and the blood-flow-noise signal SM1, displayed on the display device 60 at S8, is shorter than a length of one heartbeat-synchronous pulse, it would be impossible for the operator to judge, based on the displayed waveform or waveforms, whether the pressed portion of the carotid artery 22 suffers stenosis. Hence, the above-indicated number is so prescribed as to enable the operator to surely judge, based on the displayed waveform or waveforms, whether the pressed portion of the carotid artery 22 suffers stenosis. If a negative judgment is made at S9, S7 and the following steps are repeated.

Meanwhile, if a positive judgment is made at S9, the control goes to S10 and S11 corresponding to the blood-flow-noise-information obtaining means 76. At S10, the control device 50 determines, as the blood-flow-noise information, an average magnitude of the prescribed number of pulses of the blood-flow-noise signal SM1, received by the repetition of S7 to S9. Then, at S11, the control device 50 operates the display device 60 to display the thus determined average magnitude of the blood-flow-noise signal SM1.

Then, the control goes to S12 and S13 corresponding to the stenosis judging means 78. At S12, the control device 50 judges, if the average magnitude of the blood-flow-noise signal SM1 determined at S10 is greater than a prescribed reference value, that the pressed portion of the carotid artery 22 suffers stenosis and, if the average magnitude of the blood flow noise is not greater than the prescribed reference value, that the pressed portion of the carotid artery 22 does not suffer the stenosis. Then, at S13, the control device 50 operates the display device 60 to display the judgment made at S12. Thus, the current control cycle according to this control routine is finished.

After the control routine of FIG. 6 is finished, the pressure-pulse-wave signals SM0 will be continuously obtained by the present apparatus 10. However, if the operator judges, from the carotid pulse wave, the blood-flow-noise waveform, the blood-flow-noise information, and the judgment each displayed on the display device 60 according to the control routine, that the pressed portion of the carotid artery 22 suffers stenosis and that portion of the artery 22 is not appropriate to be pressed by the pressure-pulse-wave sensor 30, the operator will re-wear the pressure-pulse-wave detecting probe 14 at a different position on the neck portion 12.

In the embodiment in which the above-described control routine is employed, the band-pass filter 44 extracts the blood-flow-noise signal SM1 from the pressure-pulse-wave signal SM0, and the display device 60 displays the thus extracted blood-flow-noise signal SM1. Thus, the operator can judge, from the magnitude of the blood-flow-noise signal SM1 displayed on the display device 60, whether the portion of the carotid artery 22 that is pressed by the pressure-pulse-wave sensor 30 suffers stenosis.

In addition, in the embodiment in which the above-described control routine is employed, at S10 and S11 (the blood-flow-noise-information obtaining means 76), the control device 50 determines the average magnitude of the blood-flow-noise signal SM1, and the display device 60 displays the thus determined average magnitude. Thus, the operator can judge, from the average magnitude as well, whether the portion of the artery 22 pressed by the pressure-pulse-wave sensor 30 suffers stenosis.

Moreover, in the embodiment in which the above-described control routine is employed, at S12 and S13 (the stenosis judging means 78), the control device 50 judges, from the average magnitude of the blood-flow-noise signal SM1, whether the portion of the artery 22 pressed by the pressure-pulse-wave sensor 30 suffers stenosis, and operates the display device 60 to display a result of this judgment. Thus, the operator can easily know about whether the pressed portion of the artery 22 suffers stenosis.

While the present invention has been described in its preferred embodiment by reference to the drawings, it is to be understood that the invention may otherwise be embodied.

For example, in the illustrated carotid-pulse-wave detecting apparatus 10, the pressure-pulse-wave sensor 30 having the semiconductor pressure-sensing elements E in the pressing surface 42 is employed to detect a pressure pulse wave. However, it is possible to employ, for the purpose of detecting a pressure pulse wave, a semiconductor capacitive pressure sensor including an upper and a lower electrode and a silicon diaphragm sandwiched by the two electrodes. Alternatively, a pressure pulse wave may be detected using an inflatable cuff adapted to be worn on a prescribed portion of a living subject and a pressure sensor which detects a pressure in the cuff.

In the illustrated embodiment, the carotid-pulse-wave detecting apparatus 10 for detecting the pressure pulse wave produced by the carotid artery 22 is explained as a sort of pressure-pulse-wave detecting apparatus. However, the present invention is applicable to a different sort of pressure-pulse-wave detecting apparatus for detecting a pressure pulse wave produced by a different artery, for example, a radial artery.

In addition, in the illustrated carotid-pulse-wave detecting apparatus 10, each of the band-pass filter 44 and the low-pass filter 46 is provided by an electric circuit including a capacitor, etc. However, the control device 50 whose ROM 56 has a special control program pre-stored therein may be used as the band-pass filter 44 or the low-pass filter 46. That is, the band band-pass filter 44 or the low-pass filter 46 may be provided by a digital filter.

Moreover, in the illustrated carotid-pulse-wave detecting apparatus 10, the display device 60 functions as the output device. However, the display device 60 may additionally include a speaker which outputs, as the output device, a sound representing the waveform of the noise signal SM1 extracted by the band-pass filter 44. The speaker may also be used to output a sound representing the result of judgment of the stenosis judging means 78.

The stenosis judging means 78 judges whether the blood-flow-noise information is greater than a prescribed reference value and thereby judges whether the pressed portion of the carotid artery 22 suffers stenosis. However, the stenosis judging means 78 may obtain, in the same manner as that in which the blood-flow-noise information is obtained, pressure-pulse-wave information or carotid-pulse-wave information representing a magnitude of the pressure-pulse-wave signal SM0 or the carotid-pulse-wave signal SM2, and determine a ratio of the blood-flow-noise information to the pressure-pulse-wave information or carotid-pulse-wave information. In the latter case, the stenosis judging means 78 may judge whether the thus determined ratio is greater than a prescribed reference value and thereby judge whether the pressed portion of the artery 22 suffers stenosis.

Moreover, in the embodiment in which the above-described control routine is employed, the display device 60 displays the three sorts of information from each of which the operator can judge whether the pressed portion of the artery 22 suffers stenosis, that is, the blood-flow-noise waveform, the average magnitude of the blood-flow-noise signal SM1 (i.e., the blow-flow-noise information), and the result of judgment. However, the display device 60 may be so modified as to display only one or two of the three sorts of information.

While the present invention has been described in detail in its embodiments by reference to the drawings, it is to be understood that the present invention is not limited to those details of the described embodiments and may be embodied with other changes and improvements that may occur to a person skilled in the art without departing from the spirit and scope of the invention defined in the appended claims.

What is claimed is:

1. An apparatus for detecting a pressure pulse wave produced by an artery of a living subject, comprising:

a pressure-pulse-wave sensor which is adapted to be pressed against the artery of the subject via a skin of the subject, detects the pressure pulse wave produced by the artery, and generates a pressure-pulse-wave signal representing the detected pressure pulse wave;

a band-pass filter which extracts, from the pressure-pulse-wave signal, a blood-flow-noise signal having frequencies in a prescribed blood-flow-noise frequency range; and an output device which outputs the blood-flow-noise signal extracted by the band-pass filter.

2. An apparatus according to claim 1, wherein the band-pass filter extracts, from the pressure-pulse-wave signal, the blood-flow-noise signal having the frequencies in the prescribed blood-flow-noise frequency range which ranges from 200 Hz to 600 Hz.

3. An apparatus according to claim 1, wherein the output device comprises a display device which displays, in a two-dimensional screen thereof, a waveform of the blood-flow-noise signal extracted by the band-pass filter.

4. An apparatus according to claim 3, wherein the display device displays, in the two-dimensional screen thereof, a waveform of the pressure-pulse-wave signal generated by the pressure-pulse-wave sensor, such that the waveform of the blood-flow-noise signal extracted by the band-pass filter is comparable with the waveform of the pressure-pulse-wave signal.

5. An apparatus according to claim 1, wherein the output device comprises a speaker which generates a sound representing a waveform of the blood-flow-noise signal extracted by the band-pass filter.

6. An apparatus according to claim 1, wherein the pressure-pulse-wave sensor comprises at least one semiconductor pressure-sensing element which is adapted to be pressed against the artery of the subject via the skin of the subject, detects the pressure pulse wave produced by the artery, and generates the pressure-pulse-wave signal representing the detected pressure pulse wave.

7. An apparatus according to claim 1, wherein the pressure-pulse-wave sensor comprises an inflatable cuff which is adapted to be wound around a body portion of the subject and is inflated to press the artery of the subject via the skin of the subject, so that the cuff detects the pressure pulse wave produced by the artery, and provides the pressure-pulse-wave signal representing the detected pressure pulse wave.

8. An apparatus for detecting a pressure pulse wave produced by an artery of a living subject, comprising:

a pressure-pulse-wave sensor which is adapted to be pressed against the artery of the subject via a skin of the subject, detects the pressure pulse wave produced by the artery, and generates a pressure-pulse-wave signal representing the detected pressure pulse wave;

a band-pass filter which extracts, from the pressure-pulse-wave signal, a blood-flow-noise signal having frequencies in a prescribed blood-flow-noise frequency range;

a blood-flow-noise-information obtaining means for obtaining blood-flow-noise information representing a magnitude of the blood-flow-noise signal extracted by the band-pass filter; and an output device which outputs the blood-flow-noise information obtained by the blood-flow-noise-information obtaining means.

9. An apparatus for detecting a pressure pulse wave produced by an artery of a living subject, comprising:

a pressure-pulse-wave sensor which is adapted to be pressed against the artery of the subject via a skin of the subject, detects the pressure pulse wave produced by the artery, and generates a pressure-pulse-wave signal representing the detected pressure pulse wave;

a band-pass filter which extracts, from the pressure-pulse-wave signal, a blood-flow-noise signal having frequencies in a prescribed blood-flow-noise frequency range;

a stenosis judging means for making, based on a magnitude of the blood-flow-noise signal extracted by the band-pass filter, a judgment about whether a portion of the artery that is pressed by the pressure-pulse-wave sensor suffers stenosis; and an output device which outputs the judgment made by the stenosis judging means.

10. An apparatus according to claim 9, wherein the stenosis judging means makes a judgment that the portion of the artery that is pressed by the pressure-pulse-wave sensor suffers the stenosis, when the magnitude of the blood-flow-noise signal extracted by the band-pass filter is greater than a reference value.

* * * * *